(12) United States Patent
Hiraiwa

(10) Patent No.: US 10,272,104 B2
(45) Date of Patent: Apr. 30, 2019

(54) METHOD FOR TREATING ITCH

(71) Applicant: Lilac Laboratory Co., Ltd., Saitama-ken (JP)

(72) Inventor: Ryoichi Hiraiwa, Saitama-ken (JP)

(73) Assignee: Lilac Laboratory Co., Ltd., Saitama-ken (JP)

( * ) Notice: Subject to any disclaimer, the term of this patent is extended or adjusted under 35 U.S.C. 154(b) by 185 days.

(21) Appl. No.: 15/138,229

(22) Filed: Apr. 26, 2016

(65) Prior Publication Data

US 2016/0235784 A1   Aug. 18, 2016

Related U.S. Application Data

(62) Division of application No. 14/799,591, filed on Jul. 15, 2015, now abandoned.

(30) Foreign Application Priority Data

Jul. 20, 2014 (JP) ................................. 2014-160819

(51) Int. Cl.
*A61K 33/06* (2006.01)
*A61K 31/716* (2006.01)
*A61K 9/00* (2006.01)
*A61K 9/14* (2006.01)
*A61K 31/724* (2006.01)

(52) U.S. Cl.
CPC ............ *A61K 33/06* (2013.01); *A61K 9/0014* (2013.01); *A61K 9/14* (2013.01); *A61K 9/143* (2013.01); *A61K 9/146* (2013.01); *A61K 31/716* (2013.01); *A61K 31/724* (2013.01)

(58) Field of Classification Search
CPC ......... A61K 8/738; A61K 33/06; A61Q 15/00
See application file for complete search history.

(56) References Cited

U.S. PATENT DOCUMENTS

| 5,780,020 A | 7/1998 | Peterson et al. |
| 5,861,143 A * | 1/1999 | Peterson ................ A61K 8/738 |
| | | 422/5 |
| 2004/0131696 A1* | 7/2004 | Buchalter ............ A61K 9/0048 |
| | | 424/617 |

FOREIGN PATENT DOCUMENTS

| JP | 2003-073249 A | 3/2003 |
| WO | WO 0149302 A1 * | 7/2001 ........... A61K 8/0208 |
| WO | 2004/035071 A | 4/2004 |

OTHER PUBLICATIONS

Topham Wood, "Home Remedies for Rashes under the Roles of Belly Fat", Aug. 16, 2013, accessed at http://www.livestrong.com/article/160837-home-remedies-for-rashes-under-the-rolls-of-belly-fat Oct. 1, 2016.*
Japanese notice of the reason for refusal dated Oct. 10, 2014.
Japanese decision of refusal dated Mar. 26, 2015.
Japanese decision to grant a patent dated Aug. 10, 2015.
Hajime Sindo, et al., Sweat allergy and Atopic dermatitis, Fragrance Journal, Japan, Fragrance Journal Ltd., May 15, 2010, 28 to 31 pages.

* cited by examiner

*Primary Examiner* — Kyle A Purdy
(74) *Attorney, Agent, or Firm* — Yokoi & Co., U.S.A.; Toshiyuki Yokoi

(57) ABSTRACT

The present invention is anti-itching powder that blocks transmission to stratum corneum and invasion up to epidermal cells by emulsion as a result of further concentration on skin stratum corneum. The emulsion is produced by mixing sweat continuously secreted during rest and sebum. The emulsion becomes a cell disorder composition. Specifically, the anti-itching powder as a fine powder contains main ingredients of aluminum chloride or alum and cyclodextrin. A fine powder as a base is dispersed into and combined with the fine powder. The application of the fine powder over the skin prevents sudden itch without blocking emission and transpiration of water in the sweat from the skin stratum corneum.

10 Claims, No Drawings

METHOD FOR TREATING ITCH

CROSS-REFERENCES TO RELATED APPLICATIONS

This patent specification is based on Japanese patent application, No. 2014-160819 filed on Jul. 20, 2014 in the Japan Patent Office, the entire contents of which are incorporated by reference herein.

BACKGROUND OF THE INVENTION

1. Field of the Invention

The present invention relates to anti-itching powder to outstandingly prevent skin diseases such as eczema and dermatitis.

2. Description of Related Art

Through skin practices for 19 years, a voice of patients from which I have realized is, regardless of age, a voice questioning "Although eruption gets better with medicine, is there anything that can be done about an itch?" A dogma by dermatologists/plastic surgery doctors is that treatment of curing the eruption and soothing the itch is rules and principles derived from medical treatment for health. The medical treatment is to cure diseases. With the stereotype, the medical treatment has been developed in the form of a progress of new medicines. However, in association with a recent expansion of medical cost, approaches to prevent diseases before getting sick have been gradually taken into consideration.

Most eczema and dermatitis in the field of dermatology increase during summertime, a warm period, and a period of having a warm in a winter season. Accordingly, ways of thinking: <getting itchy due to sweating> and <Sweating aggravates the eczema and the dermatitis.> are present. However, the main cause for such sudden itch has not been solved and also has not been problematized. As a result of affection with a disease where the cause of the itch is persistently the eczema and the dermatitis, it is regarded that the main reason for causing the itch is an isolation of chemical mediators, such as histamines, from leukocytes and irritating materials such as cytokines.

Meanwhile, the way of thinking that the sweating brings the itch has been a common opinion conventionally. It has been considered that in the concept of hidroschesis, inhibiting secretion of sweat and smoothing the skin inhibit miliaria, ensuring reducing the itch. Accordingly, baby powder has been widely used as commercial products. The main ingredients of the baby powder are starch such as corn starch, zinc oxide, talc, aluminum chlorohydrate, and a similar ingredient. The principle of the baby powder is as follows. Processed starch and silicic anhydride powder absorb the sweat. The zinc oxide and the talc sterilize the skin and improve the slipperiness. The antiperspirant effect by the aluminum chlorohydrate powder inhibits the sweating. When using the baby powder after toileting the sweat on the whole body, the touch is smooth and the person feels like that the itch has subsided to some extent. However, since the itch comes back soon, the baby powder has no effect to stop a scratch action. Dermatologists recommend the baby powder as an anti-itching agent and encourage many patients who have the itch to use the baby powder. However, since the use of the baby powder does not remove the itch under the actual situation, the majority opinion is that scratches are not cleared up.

The dermatological theory up to the present sees that an emulsion composed of eccrine sweat, apocrine sweat, and sebum, which is secreted from the sebaceous gland, as a concept of moisturizing and protection effects. However, supposedly, even if water and the sebum have gone from the skin stratum corneum, as long as the epidermal cells themselves are not damaged, the skin is merely dried to the extent where the sulcus cutis looks white macroscopically. Functions such as stretchability of the epidermal cell layer are not lost at all. This is because that the stratum corneum serves as a barrier for the living epidermal cells.

Additionally, the generally spoken term, <dry skin> is extremely ambiguous. By appearance of eczema (dermatitis) of almost 100%, the originally living epidermal cells themselves are disordered, and extinct epidermal cells (scales), which lose their nuclei, are deposited. This state is merely referred to as the dry skin or xeroderma. As a result of extensive researches based on such knowledge, the inventor has found that this emulsion itself is a causative agent mainly causing the sudden itch. Thus, the inventor has reached the present invention.

The present invention provides anti-itching powder. The anti-itching powder prevents the emulsion, which is produced by mixing sweat, which is continuously secreted during rest (referred to as persistent sweat) and the sebum and becomes a cell disorder composition, from transmitting the stratum corneum and invading the epidermal cells as a result of further concentration on the skin stratum corneum. Specifically, the present invention provides the anti-itching powder that outstandingly prevents the skin diseases, such as the eczema and the dermatitis, without blocking emission and transpiration of the water in the sweat from the skin stratum corneum. The anti-itching powder is fine powder whose main ingredients are an astringent, such as an aluminum chloride compound and alum, and cyclodextrin.

BRIEF SUMMARY OF THE INVENTION

The following describes a basic structure and a prescription example of anti-itching powder of the present invention. With respect to powder of 100 g, which becomes a base, approximately 2 to 15% of aluminum chloride hexahydrate, anhydrous aluminum chloride, or the mixture of them, which will be the main ingredient, is incorporated with and combined with cyclodextrin (hereinafter referred to as CD), which is similarly the main ingredient, for production. The CD is an inclusion compound that can include a hydrophobic material, such as the sebum and the emulsion, by meeting a certain condition. In the present invention, the CD mainly means $\alpha$-CD, $\beta$-CD, $\gamma$-CD, and the mixture composition of these materials. Besides, inclusion compounds other than the CD, which is the derivative of $\alpha$-CD, $\beta$-CD, and $\gamma$-CD, can also be used. However, as the precondition, as long as the inclusion compound absorbs the emulsion containing the sebum and dissolves the emulsion into water, all inclusion compounds can be used. Since the absorption condition changes depending on a solute to be added, it is preferable to select and use the inclusion compound so as to establish an optimal condition.

As the aluminum chloride, both the anhydrous aluminum chloride and the aluminum chloride hexahydrate can be used. Besides, although the effect is inferior, a polymer such as burnt alum and basic aluminum chloride can also be used. As one example, combining the polymer around 10 to 20% with respect to a powder basic base of 100 g is preferable. However, the polymer is disadvantageous in short durability of functionality, around one-third of the aluminum chloride. Besides, the hydrate of the alum can be similarly used. It is preferable that the raw material of the powder basic base has a composition similar to the baby powder. However, the use of zinc oxide powder, which has an effect to protect roots of hair from an influence of solar light, especially ultraviolet rays, or a similar material, and besides talc powder, starches, a celluloses such as HPC, MC, and CMC, and the mixture of them as a single basic base does not bring any problem in effect and a big harmful effect.

The usual moisturizer and an antioxidant substance, which is also a moisture composition, such as vitamin E and ascorbic acid 2-phosphate, are preliminary powdered with powdering assistant, such as the CD and silicic anhydride. The powdered antioxidant substance can also be appropriately selected and combined.

The following methods for applying the anti-itching powder are applicable. The anti-itching powder is thinly applied to the skin surface directly with a puff so as to stroke the skin surface. Alternatively, the anti-itching powder is applied to the skin surface so as to lightly press the skin surface with the pulps or the palm. Alternatively, although there is an adverse effect of suction, a method for application by a spray method with high pressure gas or a similar method is also simple.

DETAILED DESCRIPTION OF THE INVENTION

The following describes an aggressive factor related to an appearance of sudden itch not due to dermatitis and a mechanism of production of an aggressive material in detail. There are two main factors to cause sudden itching to appear, regardless of presence of an inflammation on a skin. The one factor is persistent sweat mainly secreted from apocrine sweat glands and eccrine sweat glands. Although the composition is mainly the water, the persistent sweat contains salt, even a trace of which becomes a stimulatory composition to the skin, uric acid, lactic acid, butyric acid, isovaleric acid, unsaturated aldehyde, and amines, which are produced by zymolysis of adhered bacteria and indigenous dermal bacteria. The other is sebum, which is unsaturated fatty acids secreted from sebaceous glands, and steroids. It is considered that when these aggressive factors are concentrated on stratum corneum and become a concentrated emulsion, the aggressive factors turn into the aggressive materials.

The mechanism of action is caused when the aggressive material meets the condition: (A) or (B) or (A)+(B).
(A) The aggressive material soaks into deep parts of epidermal cells and directly stimulates the Meissner's corpuscle, which is an end of a sensory nerve (C-fiber).
(B) When the aggressive material directly penetrates to the inside of the cells from the epidermal cell membrane, the cells themselves sense the aggressive material as an abnormal signal, and the result is recognized as itching.

The emulsion is an epidermal cell disorder composition produced with the sweat and the sebum. The emulsion, which is produced with the persistent sweat and the sebum, is further concentrated on the stratum corneum. Consequently, the emulsion transmits the stratum corneum and soaks up to the epidermal cells, thus inducing the itching. Fine powder containing aluminum chloride and cyclodextrin as the main ingredients and talc, starch, cellulose, zinc oxide, titanium oxide, or a similar material as the basic bases is combined with fine powder, which will be the main ingredient. The anti-itching powder thus formed is applied over the skin face. This instantly hardens the stratum corneum epidermidis. This constructs porous, degenerative stratum corneum that does not transmit and block the transpiration of water. This porous, degenerative stratum corneum causes a complex barrier to accumulate this emulsion. The complex barrier is constructed with the aluminum chloride, the cyclodextrin, and the water from sweat. Accordingly, the emulsion cannot penetrate up to the epidermal cells, the itching is not initiated.

Once applying the anti-itching powder ensures maintaining the skin surface of the stratum corneum always smooth. On a facial surface where the secretion of the sebum is particularly large, after an elapse of roughly 12 hours, an amount of absorption of the emulsion in the complex is likely to decay. Therefore, although a slightly sticky texture appears, even after an elapse of seven days, the itch does not occur. The reason is considered as follows. The formation of the complex barrier theoretically continues blocking the mechanism of emulsion production on the stratum corneum epidermidis until a turnover cycle of the epidermis. However, the entire skin surface constantly receives some sort of physical friction from, for example, clothes and a towel. Accordingly, around 36 hours is actually regarded as a limit for practical use.

When the accumulation of the emulsion by the complex barrier decays and is saturated, and an equilibrium state is reached, extra emulsion and newly produced sebum are oozed out to the stratum corneum surface. This phenomenon is caused by a surface-active effect generated on the interface of the stratum corneum. The phenomenon is considered to be caused by CD molecules filmy aligning with their hydrophobic faces (guest holes) downward and their hydrophilic groups upward. This generates an action and an effect of the hydrophilic group shedding the sebum and the sweat. Additionally, the persistently secreted sebum does not exhibit a stickily touch, but is a secretion that can be lightly and easily wiped off with, for example, a tissue. The fine powder of the invention of the present application complements the effects, ensuring maintaining the feel of smoothness on the skin surface for a long time.

The application of the aluminum chloride fine powder and the cyclodextrin fine powder does not bring the action and the effect of inhibiting the sudden itch and the inflammation by themselves. However, the constitution of the emulsion barrier complex by the interaction of the degenerative stratum corneum, the aluminum chloride, the cyclodextrin, and the water expresses the mechanism of action to effectively block the cycle of the itch and the dermatitis. Accordingly, the mechanism of action can also lead to a prevention of various kinds of inflammatory skin diseases.

The invention of present application has assumed as follows. The itch that cannot be solved by the antiperspirant effect from the aluminum chloride is caused by the emulsion concentrated on the skin stratum corneum. The invention has focused on the interaction compounded by a water-repellent film effect from the aluminum chloride compound, the inclusion and absorption effects from the cyclodextrin, and the water. Thus, the invention has solved the mechanism for itch. Using the publicly-known and publicly used aluminum chloride compound as an antiperspirant, numerous sweating tests have been conducted. For example, the water solution of the aluminum compound is applied over the whole body, and a heat accumulation test has been conducted. From the result of the heat accumulation test, the following features have been proved. The main effect is not the antiperspirant effect but the water repellent effect. Further, the porous thin film, which easily transmits the sebum and the water, is formed. The invention has an effect of forming not only the degenerative stratum corneum but also a water-repellent film to a different solute in the water solution. The water-repellent film establishes a mechanism as if an interfacial phenomenon where the water is peeled from the solute occurs and this blocks the water. The following is considered. This mechanism acts as an effect to block the production of the emulsion, which will be the causative agent of itch. Alternatively, the mechanism demulsifies the emulsion and isolates the water and the sebum. Thus, the mechanism promotes the inclusion and absorption effects of the sebum with the cyclodextrin. The cyclodextrin that has absorbed and included the sebum forms free water and a colloidal emulsion. However, the concentration of water on the degenerative stratum corneum promotes a condensation effect and the cyclodextrin is gelatinized. This brings a favorable condition to absorb and secure the aqueous (Some of them are possibly oily.) causative agent of itch to between particles and the periphery of the CD. According to this, it is concluded that the itch is prevented. Thus, the present invention has been completed. Regarding this itch prevention effect, the itch prevention effect cannot be obtained in examples of single use of the respective aluminum chloride and cyclodextrin, which are described in detail in itch prevention effect experiment, which will be described later.

<Working Example 1>conducted heat accumulation experiment with the anti-itching powder. With the anti-itching powder applied over the whole body, two tested persons, male and female, climbed a mountain and run to test for how much the heat accumulation occurs. The result is as follows.

1) During climbing: The tested persons completed a low mountain at the altitude of 380 m for about two and half hours back and forth. The external temperature was 27° C., and the humidity was 75%.

The tested person (male): The body temperature after the exercise was 34.5 to 35.0° C., and the temperature before the climbing was 35.1 to 35.8° C.

The tested person (female): The body temperature after the exercise was 34 to 34.5° C., and the temperature before the climbing was 34.5 to 34.7° C.

2) During running for 10 km: The tested persons completed the running for about one hour. The external temperature was 30° C., and the humidity was 73%.

The tested person (male): The body temperature after the exercise was 34 to 35.0° C., and the body temperature before the running was 35 to 36° C.

The tested person (female): The body temperature after the exercise was 34 to 34.5° C., and the body temperature before the running was 35 to 36.2° C.

Considering from the above-described results, since both the climbing and the running involve an advantage where the sweating is significantly smooth and by a distinguished water repellent effect, the sweat is likely to flow, an increase in the body temperature was not initiated. That is, it has been proved that even if the anti-itching powder of the present invention is applied over the whole body, a state where the skin is not physiologically changed at all from the usual skin can be maintained.

<Experimental Example of Itch Prevention Effect>
Details of Experiment
Purpose of Experiment The fine powder of the aluminum chloride hexahydrate and the cyclodextrin (referred to as the CD) were each used alone for application to the skin over the whole body. From the result, whether the itch prevention effect was able to be bodily sensed or not was determined through somesthetic testing.
Participated Examinees three (male: 2, female: 1)
Testing Method Fine powder compositions of Experiment 1 to Experiment 3 were applied to the skin over the whole body. The climbing of a low mountain (altitude: 300 to 400 m) of 2 to 20 km and running of 2 to 15 km were executed 100 times appropriately for all seasons and for two years with the respective samples. Whether the itch was clearly removed or not and the appearance of the itch was able to be prevented or not were measured setting eight hours from the test start as terminal time. During the period, the somesthetic testing was conducted for determination. The total count of itches developed without application of various kinds of fine powder agents to the skin over the whole body (the head, the face, the body, and the entire feet) was set to 100. The degree of the itch was indicated by a "proportion of itch."

Experiment 1. The somesthetic testing was conducted to determine whether the single use of the aluminum chloride fine powder was able to prevent the itch or not based on the following prescription example. The result is shown in the following. First, since the moisture absorption and the deliquescency are large, pulverization of the aluminum chloride hexahydrate is difficult. Moreover, for direct application to the skin, the aluminum chloride hexahydrate has a high pH and therefore initializes a skin disorder. Accordingly, as the fine powder base, which will be the basic, fine powder formed by combining the aluminum chloride hydrate was used to determine the itch prevention effect by the somesthetic testing. The following fine powder base, which becomes the basic, was employed. Commercially available 160-mesh pass activated zinc oxide of 40 g, talc of 40 g, and 100-mesh pass corn starch of 20 g were used. Powdery aluminum chloride hydrate of 15 g was combined with these materials. The combined material was crushed and mixed for 25 minutes with ball mill. The material was shaken with a 48-mesh screen to produce mixed fine powder.

<Result>The proportion of itch was 99%. The itch was hardly removed.

Experiment 2. The somesthetic testing was conducted to determine whether the single use of the cyclodextrin was able to prevent the itch or not based on the following four prescription examples. The result is shown in the following.

1. α-CD The result of testing the application of the fine powder alone to the skin over the whole body
<Result>The proportion of itch was 100%. The itch was not removed. Feel of stickiness of the sweat over the whole body was strong, and the itch was not removed.

2. β-CD The result of testing the application of the fine powder alone to the skin over the whole body
<Result>The proportion of itch was 100%. Feel of stickiness of the sweat over the whole body was strong, and the itch prevention effect was not able to be bodily sensed.

3. γ-CD The result of testing the application of the fine powder alone to the skin over the whole body
<Result>The proportion of itch was 100%. Feel of stickiness of the sweat over the whole body was strong, and the itch prevention effect was not able to be bodily sensed.

4. The result of conducting the somesthetic testing by application of a material formed by adding and mixing the fine powder β-CD of 10 g to a basic base of 100 g to the skin over the whole body
<Result>The proportion of itch was 100%. Although the feel of stickiness was significantly reduced, the itch prevention effect was not able to be bodily sensed.

Experiment 3. Based on <Working Example 1> of the invention of the present application, the aluminum chloride and β-CD as the main ingredients were combined with the fine powder base, which becomes the basic. The anti-itching powder thus formed was applied to the skin over the whole body to conduct the somesthetic testing. The result is as follows. The test results using the α-CD and the γ-CD had no significant difference.

<Result>As the average value of the three examinees, the proportion of itch was in a range of 30 to 0, and the persons felt that the itch was restricted in the 70 percent of the entire test result.

In 30 percent of the results among them, the proportion of itch was 5% or less.

<Consideration> To conduct the above-described test, it is considered that the state of the skin is not constant through the year and is affected by temperature/humidity conditions of the external air to some extent. However, even considering errors, the itch prevention effect has been verified from the experiment result of the anti-itching powder of the invention of the present application.

The anti-itching powder of the present invention has an advantage that can be used also during treatment with an ointment or a similar medicine. In some cases, this reduces a usage frequency of curative medicine and duration of treatment. It is also possible to present an optimal, satisfactory periods of use or to propose a new usage method also for diseased patients who dislike steroids for external application. The following further describes problematic diseases with concrete examples in detail.

The application of the anti-itching powder composited with the main ingredients of the aluminum chloride and the cyclodextrin over the whole body reduces the stickiness on the skin surface and reduces a shine. For example, before bathing or after bathing, the anti-itching powder is applied over the entire facial surface. Even after the elapse of several hours, the entire forehead is smooth and the rash skin touch disappears.

The accumulation of the sebum in pores (drops of sebum, lumps of sebum, and grains of sebum) on a nose, which is easily recognized, outstandingly reduces. The continuous application to the precordium and the shoulders to the back allows feeling apparent reduction in acnes and disappearance of the acnes. The reasons are considered as follows. The anti-itching powder of the present invention inhibits: 1) the expression of sudden itching and 2) penetration of the emulsion, which is constituted of the sweat and the sebum, related to an appearance of acute-phase folliculitis into the living epidermal cell layer and cells on a wall of hair follicle (a wall of the pores).

Besides, although there are countless various kinds of inflammatory skin diseases, the initial lesion is papular dermatitis, and the target is mainly the roots of hair. Apart from the seriousness of the dermatitis and whether the sudden itch is noticed or not, with the papular dermatitis, the sudden itch is preceded. After an elapse of certain time, the dermatitis develops into papules. To scratch these papules, the healthy skin around the papules, which is not directly related to the papules, is also scratched, resulting in expansion of the disease.

Further, the strength of scratch, whether the skin is strongly scratched by tiptoes, the skin is scratched so as to rub the skin by the pulps, the skin is scratched with a towel, or the skin is scratched over clothes; how long is the skin scratched and how long is the period of scratch; and under these situations, how long period and how strong extent the dermatitis keep occurring. These situations design and initialize various and variety of inflammatory skin diseases.

The following describes the embodiments of the present invention.

WORKING EXAMPLE 1

The aluminum chloride hexahydrate of 7 g and β-CD of 10 g were introduced into a ceramic ball mill together with the powder basic base of 100 g and were crushed around 15 minutes. Thus, as the 48-mesh pass crushed mixture, the anti-itching powder was obtained. The zinc white of 40 g, the talc of 40 g, and the corn starch of 20 g were combined to produce the powder basic base.

WORKING EXAMPLE 2

The aluminum chloride hexahydrate of 5 g and β-CD of 5 g were introduced into the ceramic ball mill together with the powder basic base of 100 g and were crushed and mixed for 15 minutes. Thus, as the 48-mesh pass crushed mixture, the anti-itching powder was obtained. The zinc white of 50 g, the talc of 20 g, and the corn starch of 30 g were combined to produce the powder basic base.

WORKING EXAMPLE 3

Aluminum chloride anhydrate of 5 g and each 4 g of α-CD, β-CD, and γ-CD, 12 g in total, were introduced to a mixer together with the powder basic base of 100 g and were mixed for 5 minutes. Thus, the anti-itching powder was obtained. The talc of 60 g, the corn starch of 30 g, silicic anhydride of 5 g, and sodium oxide of 5 g were combined to produce the powder basic base.

WORKING EXAMPLE 4

Anhydrous alum of 20 g and β-CD of 5 g were introduced into the mixer together with the powder basic base of 100 g to obtain 65-mesh pass anti-itching powder. The zinc white of 40 g, the talc of 30 g, and the corn starch of 30 g were combined to produce the powder basic base.

WORKING EXAMPLE 5

The aluminum chlorohydrate of 10 g and α-CD of 10 g were introduced to the ceramic ball mill together with the powder basic base of 100 g and were crushed around 25 minutes. Thus, as the 48-mesh pass crushed mixture, the anti-itching powder was obtained. The zinc white of 40 g, the talc of 40 g, and the corn starch of 20 g were combined to produce the powder basic base.

WORKING EXAMPLE 6

The aluminum chloride hexahydrate of 7 g and β-CD of 10 g were introduced to the ceramic ball mill together with the powder basic base of 100 g and were crushed around 15 minutes. Thus, as the 48-mesh pass crushed mixture, the anti-itching powder was obtained. The zinc white of 40 g, the talc of 40 g, and the corn starch of 20 g were combined to produce the powder basic base.

WORKING EXAMPLE 7

The aluminum chloride hexahydrate of 7 g and γ-CD of 8 g were introduced to the ceramic ball mill together with the powder basic base of 100 g and were crushed around 15 minutes. Thus, as the 48-mesh pass crushed mixture, the anti-itching powder was obtained. The zinc white of 40 g, the talc of 40 g, and the corn starch of 20 g were combined to produce the powder basic base.

WORKING EXAMPLE 8

The anhydrous alum of 20 g and β-CD of 10 g were introduced to the ceramic ball mill together with the powder basic base of 100 g and were crushed around 15 minutes. Thus, as the 48-mesh pass crushed mixture, the anti-itching powder was obtained. The zinc white of 40 g, the talc of 40 g, and the corn starch of 20 g were combined to produce the powder basic base.

The emulsion is the cell disorder composition, which becomes an ignition factor of acute inflammation or triggers the acute inflammation, or the emulsion causes a growth of bacteria and smell. Inhibiting the production of the emulsion for a certain period of time (around 36 hours to two weeks) provides the following effects.

Except for the emulsion, as the factors for the pores to cause the inflammation, which is a part of a transition process to the dermatitis of the pores, influences from the ultraviolet rays, the steroid, and reactive oxygen have been known. However, the generation of the reactive oxygen means that the cell disorder has already been initialized from any cause.

1. The anti-itching powder inhibits a sequence of cycles of inflammation where the inflammation that has once occurred in the pores persists and then is reinforced little by little. It is said that a chain of inflammation is a process of: increasing the inflammation in the pores and growing the red eminences on the pores, which is bacterial infection caused by touching and rubbing the pores. However, it is reasonable to think that the persistent penetration of the emulsion is largely related to the persistence and the aggravation of inflammation prior to secondary infection with bacteria. The process that the inflammation reaction persists and is reinforced is named as the 'cycle of inflammation.' The main factor bringing the cycle of inflammation is the emulsion.

2. The anti-itching powder has an effect of naturally regresses the red eminences, namely, the folliculitis, becoming larger on the pores. The anti-itching powder prevents the emulsion from keeping repeatedly stimulating the folliculitis. Thus, the anti-itching powder has an action and an effect that naturally flattens the red inflammatory eminences on the pores without developing the eminences into suppuration and an accumulation of pus.

3. The anti-itching powder has an effect of soothing the sudden, strong itch. The anti-itching powder has an effect of preliminary preventing the itch caused by penetration of the emulsion into the epidermis from accumulation to the stratum corneum. The anti-itching powder also has an effect of preliminary preventing the expression of sudden itch when the sweat oozes. This reduces an occasion where patients with atopy and children sweat and scratch their heads, ears, external genitalias, and limb joints. This allows bringing effects not only preliminary preventing the appearance of eczema and dermatitis but also decreasing the range.

To validate the effects, it should be considered that there are various causes as the cause of the eczema and dermatitis except for the emulsion. The causes include, for example, the ultraviolet rays, medicines (a fomentation, an external medicine, and an oral medicine), chemical substances, insects, and plants.

4. The anti-itching powder has an effect of reducing keratosis pilaris (rashes on the cheek and the arm). Although the anti-itching powder does not cure this disease itself, an acute phase before the pores are cornified is the folliculitis (acute dermatitis of the pores). A trigger factor that initializes the inflammation of the folliculitis is an accumulation of the emulsions consisted of the sweat and the sebum on the stratum corneum epidermidis around the pores. The aluminum chloride adheres to the entire stratum corneum to prevent the accumulation of the water inside the stratum corneum. So to speak, this forms the sponge-like stratum corneum epidermidis into like a single plate.

The cornification of the keratosis pilaris means that the epidermal cells at the exit of the pores go through a denaturation and change into the inflammation, lose the nuclei, and are stacked, so-called accumulation of epidermis refuses. This forms the stratum corneum epidermidis at the exit of the pores into like the single plate to inhibit the accumulation of the emulsions. This allows preventing the inflammation and the denaturation of the cells. As a result, this prevents the cornification of the pores, and consequently ensuring preventing the keratosis pilaris. The effect can be felt in a short period (one to two weeks). This is because that the inflammation of the skin leading to the keratosis pilaris is much lighter than the inflammation of the acne.

5. The anti-itching powder has an action and effect of outstandingly preventing oxidized colors of the unsaturated fatty acid secreted from the sebaceous gland, mainly yellow stains on clothing generated by the secretion of the apocrine gland.

6. The stickiness of the sweat generated by excessive sweating on the hand is not only the water but also is the emulsion consisted of the sweat and the sebum. The surface-active effect by the aluminum chloride and the CD blocks and inhibits the emulsion accumulated on the stratum corneum epidermidis. This provides a smooth texture to a person who has touched the hand.

7. The anti-itching powder with the main ingredients of the aluminum chloride and the cyclodextrin is in a category of quasi-drug. Therefore, like an insect repellent, the anti-itching powder can be casually used, anytime and anywhere regardless of frequency. Accordingly, the anti-itching powder is also excellent in convenience.

The skin-degenerative stratum corneum, the aluminum chloride, water, and the cyclodextrin construct the emulsion barrier complex. This expresses the mechanism of action to effectively block the cycle of dermatitis. This allows bringing prevention of various inflammatory skin diseases. The anti-itching powder of the present invention has an advantage that can be used also during treatment with the ointment or a similar medicine. In some cases, this substantially reduces a usage frequency of curative medicine and duration of treatment. It is also possible to present an optimal, satisfactory periods of use or to propose a new usage method also for diseased patients who dislike steroids for external application. The anti-itching powder features extremely high effectiveness as one means for alternative medicine. The anti-itching powder is an invention that provides great anticipation and prospect for treatment strategy of these diseases.

Note that, this invention is not limited to the above-mentioned embodiments. Although it is to those skilled in the art, the following are disclosed as the one embodiment of this invention.

Mutually substitutable members, configurations, etc. disclosed in the embodiment can be used with their combination altered appropriately.

Although not disclosed in the embodiment, members, configurations, etc. that belong to the known technology and can be substituted with the members, the configurations, etc. disclosed in the embodiment can be appropriately substituted or are used by altering their combination.

Although not disclosed in the embodiment, members, configurations, etc. that those skilled in the art can consider as substitutions of the members, the configurations, etc. disclosed in the embodiment are substituted with the above mentioned appropriately or are used by altering its combination.

While the invention has been particularly shown and described with respect to preferred embodiments thereof, it should be understood by those skilled in the art that the foregoing and other changes in form and detail may be made therein without departing from the sprit and scope of the invention as defined in the appended claims.

What is claimed is:

1. A method for treating itching caused by an emulsion produced by sebum and sweat, the method comprising the step of:
   applying a powder including aluminum chloride and cyclodextrin to a patient in need of treatment of skin disease associated with itch so that a complex barrier is constructed with the aluminum chloride, the cyclodextrin, and water in sweat to block a penetration of the emulsion into an epidermal cell.

2. The method for treating itching according to claim 1, wherein
   the powder further including at least one of talc, starch, cellulose, zinc oxide, titanium oxide and sodium oxide.

3. The method for treating itching according to claim 1, wherein
   the aluminum chloride included in the powder is 2 to 15% w/w with respect to the powder.

4. The method for treating itching according to claim 1, wherein the powder is applied to the skin by a puff.

5. The method for treating itching according to claim 1, wherein
   the itching is caused by inflammatory skin diseases.

6. The method for treating itching according to claim 1, wherein
   the itching is caused by eczema.

7. The method for treating itching according to claim 1, wherein
   the itching is caused by folliculitis.

8. The method for treating itching according to claim 1, wherein
   the itching is caused by atopy.

9. The method for treating itching according to claim 1, wherein
   the itching is caused by xeroderma.

10. A method for treating itching caused by an emulsion produced by sebum and sweat, the method comprising the step of:
    applying a powder including aluminum chloride and cyclodextrin to a patient in need of treatment of skin disease associated with itch to cause the following processes:
    1) constructing a complex barrier by the aluminum chloride, the cyclodextrin and water in sweat; and
    2) blocking the emulsion by the complex barrier.

* * * * *